US012685674B1

(12) United States Patent
Schwartz et al.

(10) Patent No.: US 12,685,674 B1
(45) Date of Patent: Jul. 21, 2026

(54) DYNAMIC FENESTRATION SYSTEM FOR WOUND PROTECTION AND MONITORING

(71) Applicant: University of Puerto Rico, San Juan, PR (US)

(72) Inventors: Abraham Schwartz, San Juan, PR (US); Helen M. Cruz-Munoz, San Juan, PR (US); Jeff Melendez-Rosa, Rio Grande, PR (US); Anwar Abdul-Hadi, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 19/255,125

(22) Filed: Jun. 30, 2025

(51) Int. Cl.
　　*A61F 13/02*　　(2024.01)
　　*A61F 13/00*　　(2024.01)

(52) U.S. Cl.
　　CPC　*A61F 13/0236* (2013.01); *A61F 2013/00182* (2013.01)

(58) Field of Classification Search
　　CPC .... A61F 13/02; A61F 13/023; A61F 13/0236; A61F 13/00085; A61F 2013/00182; A61F 2013/00089; A61F 2013/00582

USPC ........ 602/41, 42, 43, 58; 128/849, 853, 887, 128/888
See application file for complete search history.

(56) References Cited

U.S. PATENT DOCUMENTS 12,144,577 B1 * 11/2024 Schwartz ............... A61B 46/10

* cited by examiner

*Primary Examiner* — Caitlin A Carreiro
(74) *Attorney, Agent, or Firm* — Aldarondo IP LLC; Carlos A. Aldarondo-López

(57) ABSTRACT

A fenestration system for protecting and monitoring an injured area may have a first sheet having a first opening; a second sheet having a second opening aligned with the first opening; and a third transparent sheet positioned within a pocket formed between the first and second sheets that provides guidance to and limits the motion of the third transparent sheet. Non-elastic strings are attached to opposite ends of the third transparent sheet and can be grasped to manually move the third transparent sheet within the pocket to selectively cover or uncover the first and second openings. The system may include frames surrounding the openings, and the pocket may be formed by lateral seals maintaining proper alignment during movement and perpendicular seals limiting movement range.

20 Claims, 10 Drawing Sheets

410

411

412

DYNAMIC FENESTRATION SYSTEM FOR WOUND PROTECTION AND MONITORING

COPYRIGHT STATEMENT

BACKGROUND OF THE INVENTION

1) Field of the Invention

The invention relates in general to the field of protective medical devices, and more particularly to a dynamic fenestration system for protecting and monitoring injuries and wounds while allowing controlled access and observation.

2) Description of Related Art

Currently the state of the art includes a number of devices design to protect wounds and accelerate healing.

Exposed wounds can pose significant challenges for medical treatment and patient care. Exposure to atmospheric contaminants such as dust, smoke, or airborne pathogens creates a number of problems for the treatment of open wounds which increases the risk of infection and complications. Traditional wound dressings and bandages provide a static barrier but may impede continuous monitoring and rapid access to the injury site.

Additionally, under battlefield conditions, natural disasters, or remote locations, medical personnel often need to stabilize and transport patients for extended periods before reaching proper medical facilities. During this critical time, the ability to closely observe wounds while maintaining protection from environmental hazards is crucial for patient outcomes. However, conventional opaque bandages can delay the detection of complications like increased bleeding, infection or bone protrusion through the skin.

There is a growing interest in developing more versatile and adaptable wound protection systems that allow for both shielding from contaminants and visual assessment of injuries. Such systems could potentially improve care in challenging field conditions by enabling medical staff to monitor wounds without repeatedly exposing them to harmful atmospheric elements.

Advancements in materials science and medical device design have opened new possibilities for creating dynamic barriers that can be adjusted as needed. Incorporating transparent elements into protective coverings may allow for ongoing visual inspection while still safeguarding wounds. Additionally, mechanisms that permit controlled and temporary access to injury sites could facilitate necessary interventions without compromising overall protection.

As emergency medical care continues to evolve, there remains an opportunity to enhance wound management capabilities, particularly in non-ideal environments. Innovative approaches that balance protection, observation, and accessibility could potentially address some of the limitations of current wound care methods in the field.

These and other objects, features, and advantages of the present invention will become more readily apparent from the attached drawings and the detailed description of the preferred embodiments, which follow.

SUMMARY OF THE INVENTION

Bearing in mind the problems and deficiencies of the prior art, it is therefore an object of the present invention to provide system for providing continuous observation and rapid access and cover to protect an injured area of a patient.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to an aspect of the present disclosure, a system for providing continuous observation and rapid access and cover to an injured area of a patient is provided. The system includes three layers of transparent plastic sheets; however, any suitable material can be used. The system comprises a top sheet, a middle sheet, and a bottom sheet. The top and bottom sheets have aligned fenestrations or windows that are open and the bottom sheet provides a gap above the wound so that the middle sheet is not in direct contact with the wound being treated. The middle plastic sheet is slightly larger than the fenestrations in the top and bottom layers and has one or more non-elastic strings attached to opposed ends of the middle sheet. The middle sheet has a low coefficient of friction to provide smooth motion within the top and bottom sheets. The range of motion of the middle sheet is limited by heat seals holding the top and bottom layers together.

According to other aspects of the present disclosure, the system includes one or more of the following features. Alignment of the fenestrations may be created by pulling on the one or more strings attached to one end of the middle sheet to uncover and open the fenestration creating an open window exposing the wound. The fenestration may be closed by pulling on the one or more strings attached to the opposite end of the middle sheet. This allows the caregiver to expose the wound thereby allowing it to be inspected or treated. Then cover the fenestration by pulling on the one or more strings attached to one end of the middle sheet. The system may be attached directly to the patient or to a surgical drape.

According to another aspect of the present disclosure, the top and bottom sheets may include flexible low friction frames around the fenestrations. The middle sheet may include a frame on its borders. The frame on the middle sheet may provide a location to attach the strings used to move the middle sheet. The distance the middle sheet moves may be limited by the edge of the middle frame contacting heat seals of the top and bottom layers. Heat seals along the direction of movement may serve to keep the middle sheet aligned. These heat seals form a pocket that contains the middle sheet with the clear plastic window. Alternatively, the heat seals can be replaced with an adhesive barrier connecting the top and bottom sheets.

According to other aspects of the present disclosure, the system may include beads or other items attached to the ends of the strings to provide a physical griping entity to facilitate pulling to open or close the fenestration. The frame of the middle layer may be of a different color than the top and bottom layers to better indicate that the fenestration is open. The system may be attached via a thin double stick tape to the patient.

Also, the three layers can be attached together using double sided tape, stitching, adhesive or other fastening methods such as Velcro® or zippers positioned along the border of the fenestrations or windows.

According to another aspect of the present disclosure, the system may be configured for use in various situations, including within a sterile operating theater, in an emergency room, during patient transport by first responders, or as part of a first aid kit. The system may help retain body heat of the patient, protect and monitor injuries or wounds, and provide protection during conditions of high atmospheric contamination.

The foregoing general description of the illustrative embodiments and the following detailed description thereof are merely exemplary aspects of the teachings of this disclosure and are not restrictive.

Still other objects and advantages of the invention will in part be obvious and will in part be apparent from the specification.

The above and other objects, which will be apparent to those skilled in the art, are achieved in the present invention which is directed to a fenestration system for protecting and monitoring an injured area, comprising:

a. a first sheet having a first opening;
    b. a second sheet having a second opening aligned with the first opening;
    c. a third transparent sheet positioned between the first and second sheets, the third transparent sheet being movable relative to the first and second transparent sheets;
    d. the first and second sheets are transparent; and
    e. at least one non-elastic string coupled to the third transparent sheet for manually moving the third transparent sheet to selectively cover or uncover the first and second openings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

4

Figure 5:
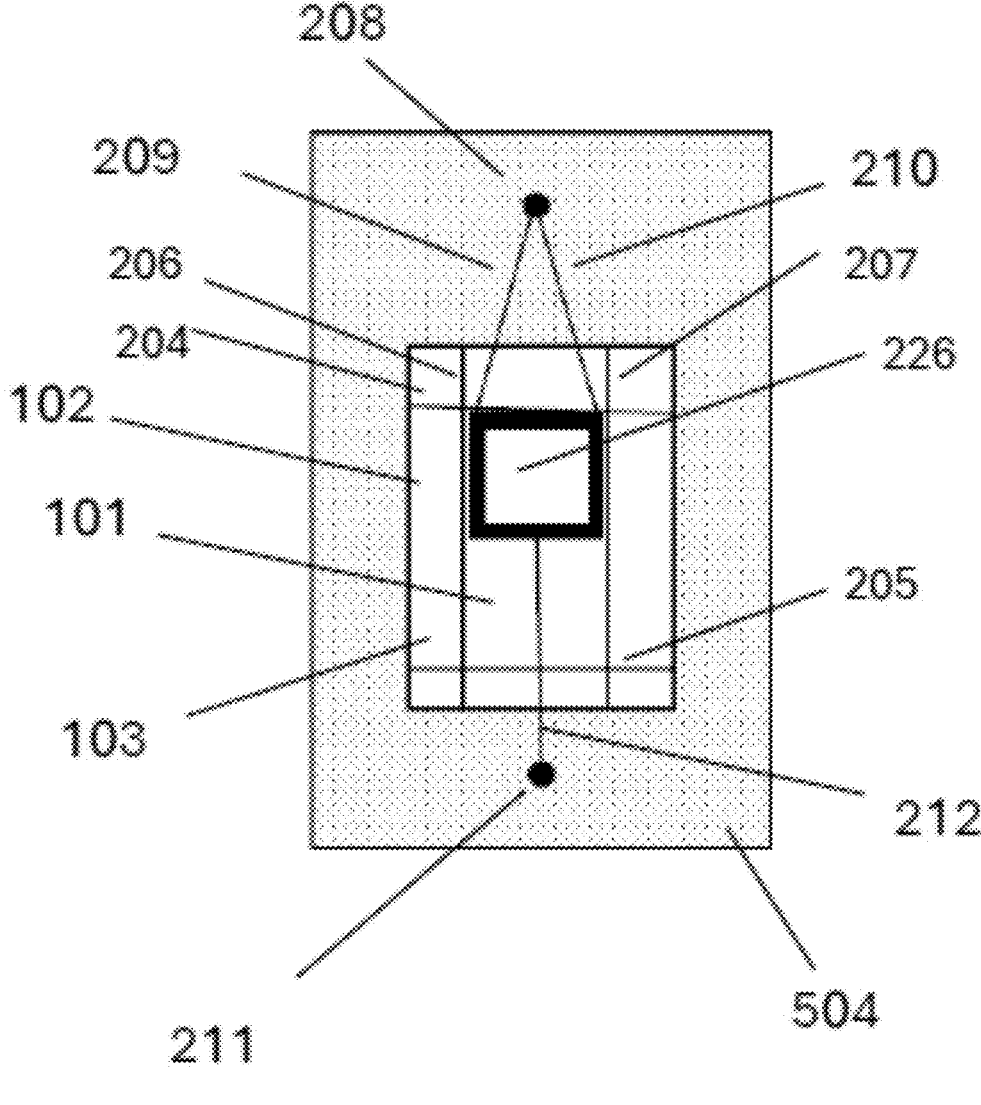

FIG. 5 illustrates a top view of the fenestration device attached to a surgical drape, according to aspects of the present disclosure.

Figure 6:
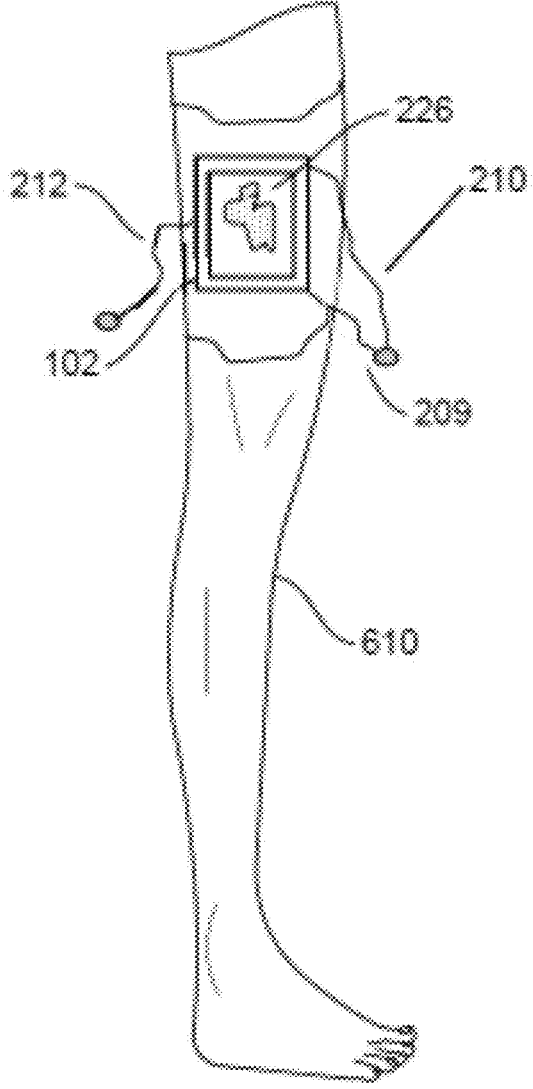

FIG. 6 illustrates an orthogonal view of the fenestration device applied to a limb, according to an embodiment.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art however that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token however, no single feature or features of any described embodiment should be considered essential to every embodiment of the invention, as other embodiments of the invention may omit such features.

In this application the use of the singular includes the plural unless specifically stated otherwise and use of the terms "and" and "or" is equivalent to "and/or," also referred to as "non-exclusive or" unless otherwise indicated. Moreover, the use of the term "including," as well as other forms, such as "includes" and "included," should be considered non-exclusive. Also, terms such as "element" or "component" encompass both elements and components including one unit and elements and components that include more than one unit, unless specifically stated otherwise.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure be considered as an example of the principles of the invention and not intended to limit the invention to the specific embodiments shown and described.

Prior to a discussion of the preferred embodiment of the invention, it should be understood that while the features and advantages of the invention are illustrated in terms of a system for providing continuous observation and rapid access and cover for an injured area of a patient's body.

The following description sets forth exemplary aspects of the present disclosure. It should be recognized, however, that such description is not intended as a limitation on the scope of the present disclosure. Rather, the description also encompasses combinations and modifications to those exemplary aspects described herein.

Figure 1:
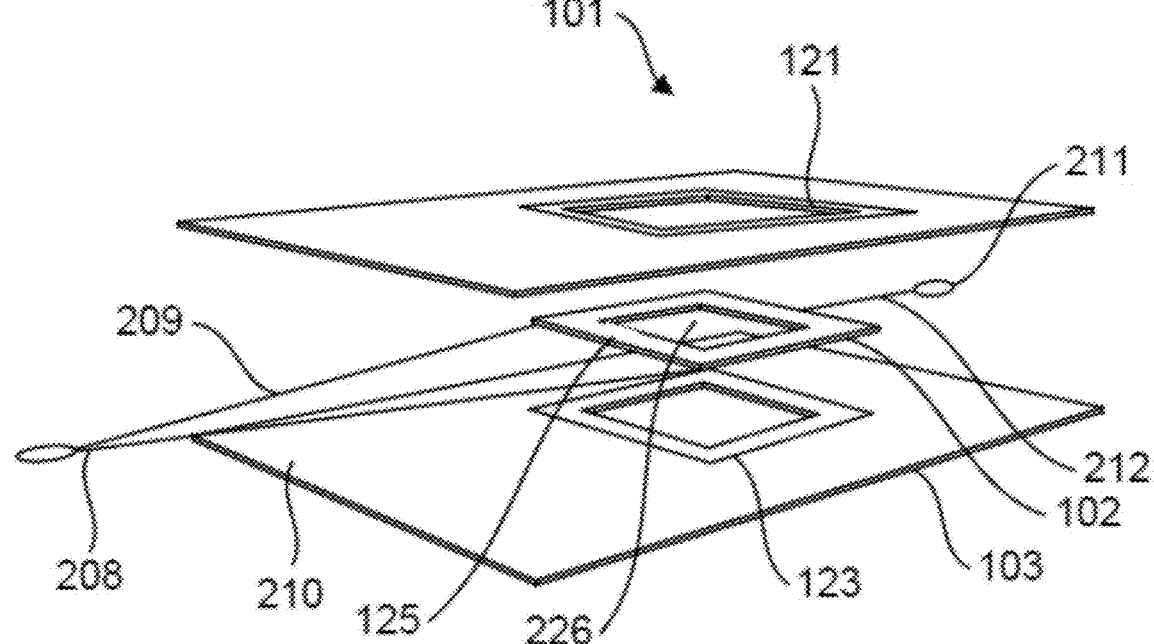
FIG. 1 shows an exploded view of a multi-layer fenestration device, according to aspects of the present disclosure.

The present disclosure relates to a dynamic fenestration system for wound protection, care and monitoring. This system includes a top plastic sheet 101, a middle plastic sheet 102, and a bottom plastic sheet 103, as shown in FIG. 1. The top plastic sheet 101 and bottom plastic sheet 103 each include a frame, specifically a top frame 121 and a bottom frame 123, respectively. The middle plastic sheet 102 incorporates a middle frame 125 with a plastic window 226. Attached to frame 125 are strings 212, 210 and 209. Strings 209 and 210 have bead 208 attached to the distal end of strings 209 and 210 and string 212 has a bead 211 attached to the distal end of string 212. In an alternative embodiment the string 212 can be replaced with two strings similar to strings 209 and 210. The top plastic sheet 101, a middle plastic sheet 102, and a bottom plastic sheet 103 can all be transparent or only the middle plastic sheet 102 can be transparent.

Figure 2:
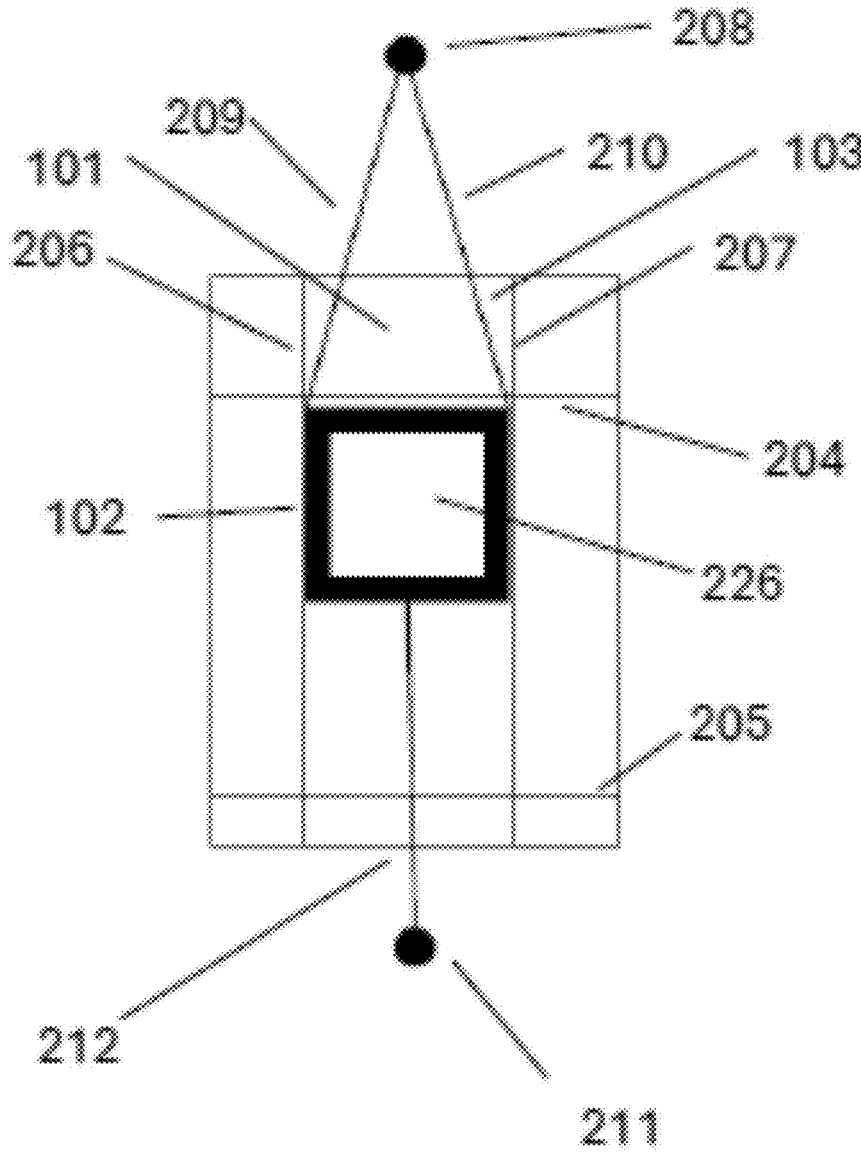
FIG. 2 illustrates a top view of a fenestration device with multiple transparent plastic sheets, according to an embodiment.

The system utilizes a string-based mechanism for controlling the movement of the middle plastic sheet 102. As illustrated in FIG. 2, this mechanism includes a first end bead 208 connected to a first string 209 and a second string 210, as well as a second end bead 211 attached to a third string 212. These strings enable manual control of the middle plastic sheet 102 position.

Figure 3A:
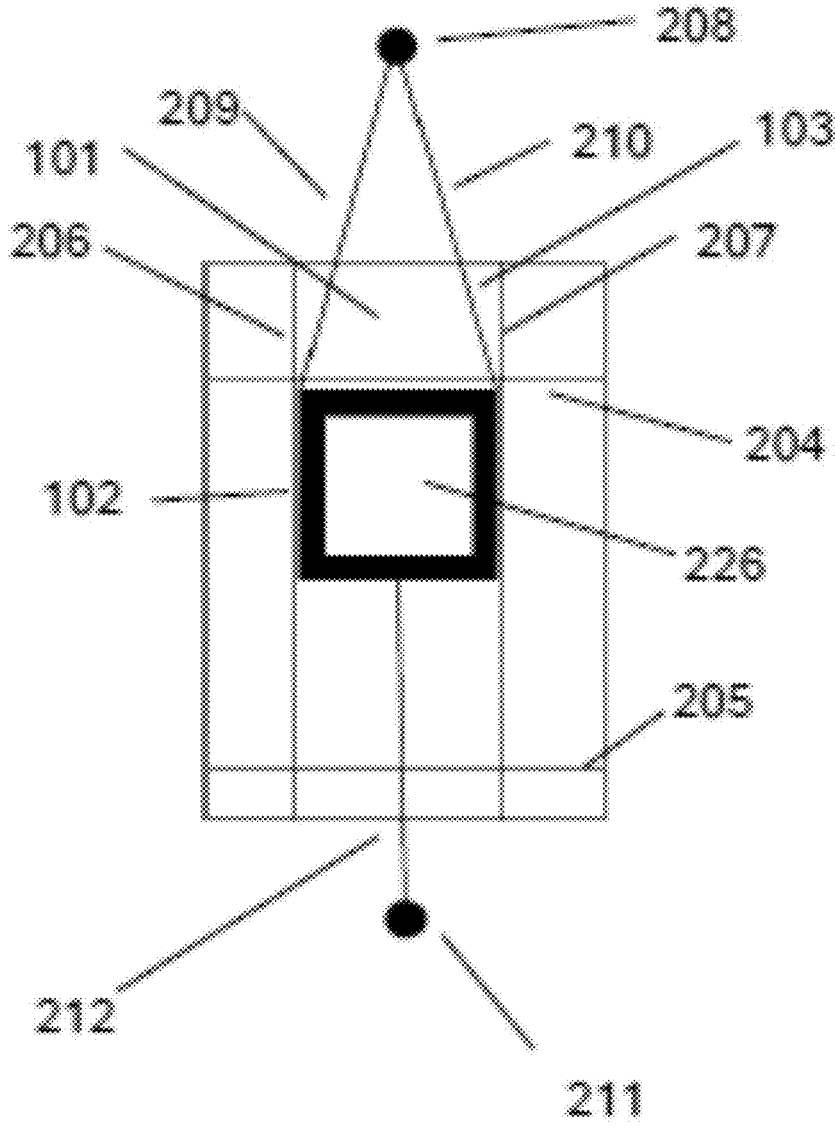
FIG. 3A illustrates a top view of the fenestration device in a closed position, according to aspects of the present disclosure.
Figure 3B:
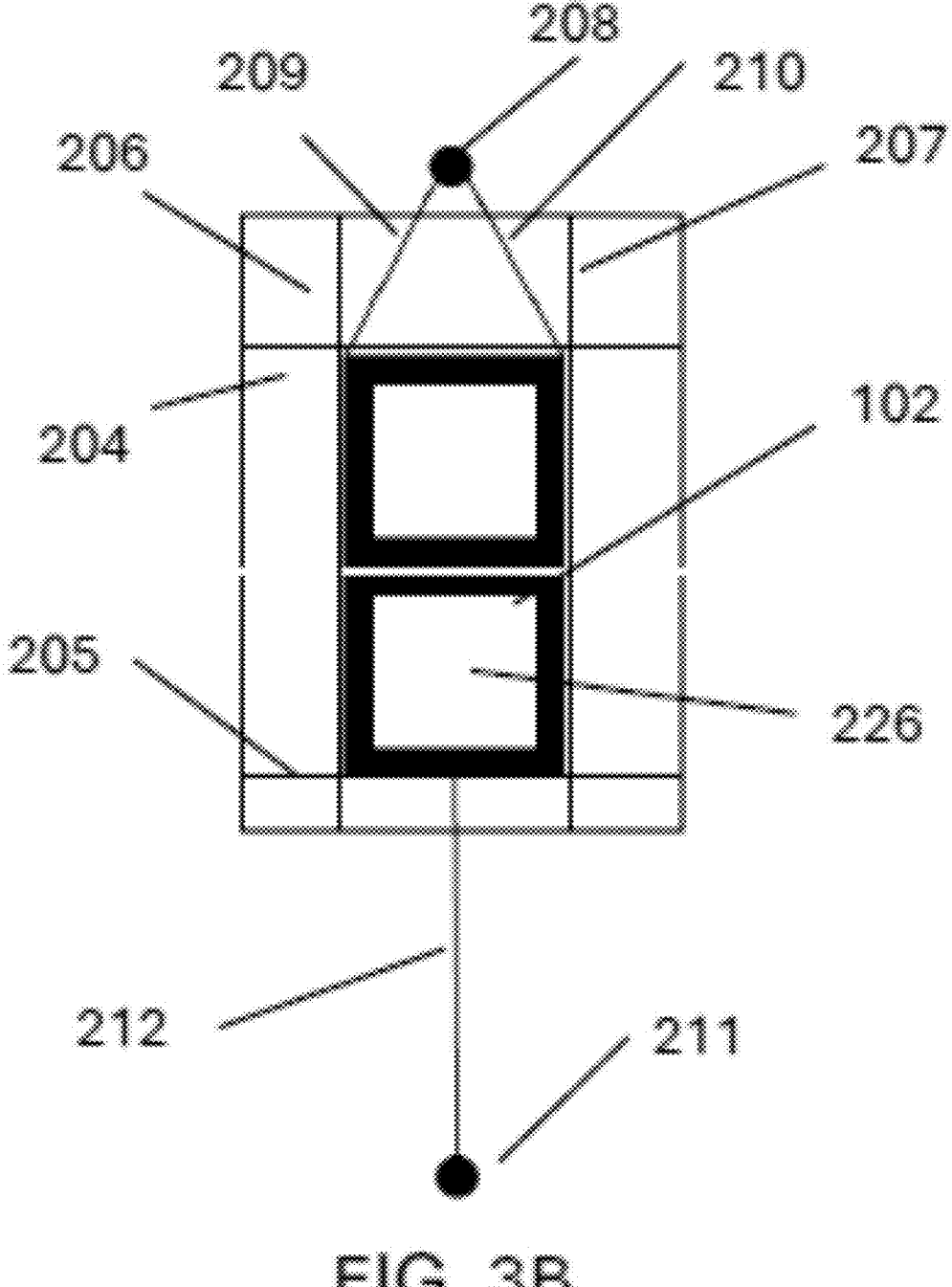
FIG. 3B illustrates a top view of the fenestration device in an open position, according to an embodiment.

To guide and limit the movement of the middle plastic sheet 102, the system incorporates seals. FIG. 3A and FIG. 3B depict a first lateral seal 204 and a second lateral seal 205 that restrict the range of motion. Additionally, a first alignment seal 206 and a second alignment seal 207 maintain proper alignment during operation.

Figure 4A:
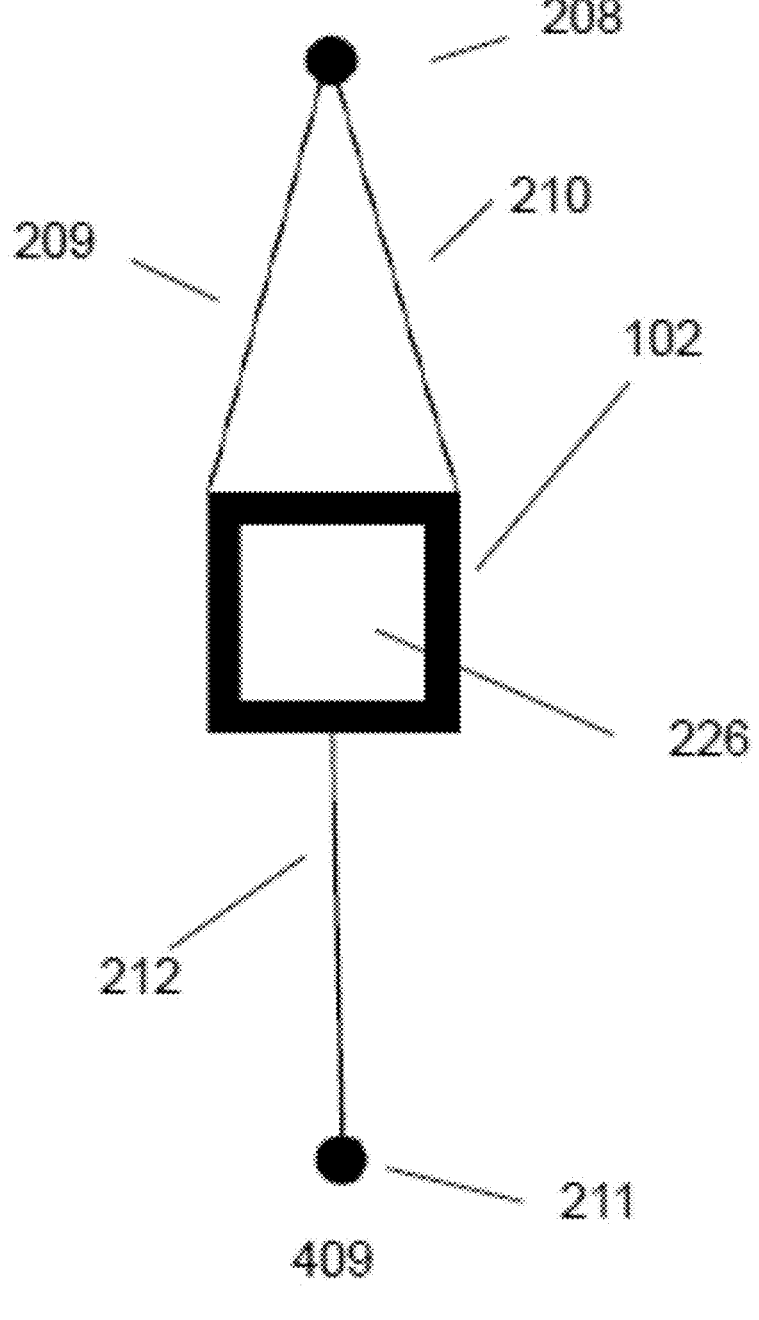
FIG. 4A illustrates a top view of the fenestration device with a square configuration, according to aspects of the present disclosure.

The system accommodates various fenestration or window shapes to suit different wound types and sizes. FIG. 4A shows a square fenestration 409, FIG. 4B displays a rectangular fenestration 410, FIG. 4C presents a circular fenestration 411, and FIG. 4D illustrates an oval fenestration 412.

For practical application, the fenestration system is designed to be used with a surgical drape 504, as demonstrated in FIG. 5. Furthermore, the system is adaptable to conform to body contours, such as a limb 610, as shown in FIG. 6.

This dynamic fenestration system provides continuous observation and rapid access to an injured area while protecting it from atmospheric and environmental contamination. The transparent nature of the plastic sheets allows for visual monitoring without compromising the sterile environment. The system is particularly beneficial because it allows the area over the surgical field to be maintained at a desired temperature such as 65 degrees F. which is crucial for wound care especially when the patient is an infant.

The dynamic fenestration system comprises multiple components that work together to provide a flexible and controllable access point for wound care and monitoring. As illustrated in FIG. 1, the system includes a top plastic sheet 101, a middle plastic sheet 102, and a bottom plastic sheet 103.

The top plastic sheet 101 and the bottom plastic sheet 103 are constructed from polyvinylchloride (PVC) with a thickness of 3 mils (thousands of an inch). Alternatively, the top plastic sheet 101 and the bottom plastic sheet 103 can be made from any suitable material that can be sterilized. These sheets incorporate the top frame 121 and the bottom frame 123, respectively. The frames are also made of PVC or any suitable material that can be sterilized and have a thickness of approximately 20 mils (thousands of an inch). The top frame 121 and the bottom frame 123 are colored and the preferred color is green to provide visual contrast. Alternatively, the frames 121 and 123 can be made from any suitable material such as nylon, PVC, ABS, polypropylene or other plastic or fiber material that can be sterilized.

The middle plastic sheet 102 includes a middle frame 125 that is covered with polyethylene (PE) or other clear plastic that can be sterilized. The middle frame 125 in one embodiment is colored red but any suitable color can be used. The use of red enhances visual differentiation from the top and bottom frames. The plastic window 226 is integrated into the middle frame 125, as shown in FIG. 2. In the preferred embodiment the middle plastic sheet 102 is made from polyethylene because sheets of PVC tend to stick to each other, therefore the middle sheet cannot have sticking properties so the middle sheet made from polyethylene slides easily between the PVC sheets.

All frames are attached to their respective plastic sheets using 3M 3400LSE 10 mm tape or another suitable tape, adhesive or fastening method such as stitches or welding of the plastic components. The attachment method must ensure a secure bond while maintaining the flexibility of the overall system. The method used to attach the frames to the sheets needs to be smooth to the sliding middle sheet.

The system utilizes a string-based mechanism for controlling the movement of the middle plastic sheet 102 and plastic window 226. As depicted in FIG. 3A and FIG. 3B, this mechanism includes a first end bead 208 connected to a first string 209 and a second string 210, as well as a second end bead 211 attached to a third string 212. These strings are made of nylon, polypropylene, or fluorocarbon providing durability and smooth operation. The beads serve as pull points for manual control of the middle plastic sheet 102 position.

To guide and limit the movement of the middle plastic sheet 102, the system incorporates seals. The first lateral seal 204 and the second lateral seal 205 restrict the range of motion. Additionally, the first alignment seal 206 and the second alignment seal 207 maintain proper alignment during operation. In one embodiment the seals are formed by heat sealing the top and bottom layers. However, the seals can be made by using adhesive to attach the top and bottom layers and thereby forming a seal the provides containment or a pocket for the middle layer. Alternatively, the layers can be attached together using double sided tape, stitching, adhesive or other fastening methods such as Velcro® or zippers positioned along the border of the fenestrations or windows.

FIG. 5 demonstrates how the fenestration system is designed to be used with a surgical drape 504. The transparent nature of the plastic sheets allows for visual monitoring of the underlying area while maintaining a sterile environment.

The system is adaptable to conform to body contours, such as a limb 610, as shown in FIG. 6. This flexibility enables the dynamic fenestration system to be effectively used on various parts of the body, providing continuous observation and rapid access to injured areas while protecting them from atmospheric contamination.

The dynamic fenestration system is assembled by stacking the top plastic sheet 101, the middle plastic sheet 102, and the bottom plastic sheet 103 in a layered configuration, as illustrated in FIG. 1. The top frame 121 and the bottom frame 123 are attached to the top plastic sheet 101 and the bottom plastic sheet 103, respectively, using 3M 3400LSE 10 mm tape or other suitable attachment device such as double-sided tape, stitching, adhesive or other fastening methods such as Velcro® or zippers. The middle frame 125 with the integrated plastic window 226 is similarly attached to the middle plastic sheet 102.

The first lateral seal 204 and the second lateral seal 205 are applied to limit the range of motion of the middle plastic sheet 102, as shown in FIG. 2. The first alignment seal 206 and the second alignment seal 207 are positioned to maintain proper alignment during operation. These seals are created through heat sealing processes or by using double side tape or adhesive to attach the top and bottom layers together to for the seal and the resulting pocket for the middle plastic sheet 102.

The string system for controlling the movement of the middle plastic sheet 102 is assembled by attaching the first string 209 and the second string 210 to the first end bead 208, and the third string 212 to the second end bead 211. These strings are then connected to the middle frame 125 of the middle plastic sheet 102.

To operate the dynamic fenestration system, a user pulls on the first end bead 208 or the second end bead 211. Pulling the first end bead 208 slides the middle plastic sheet 102 in one direction, closing the fenestration by aligning the plastic window 226 with the openings in the top plastic sheet 101 and the bottom plastic sheet 103, as depicted in FIG. 3A. Conversely, pulling the second end bead 211 slides the middle plastic sheet 102 in the opposite direction, opening the fenestration by positioning the plastic window 226 away from the openings, as shown in FIG. 3B.

The system accommodates various fenestration shapes, including the square fenestration 409 (FIG. 4A), the rectangular fenestration 410 (FIG. 4B), the circular fenestration 411 (FIG. 4C), and the oval fenestration 412 (FIG. 4D). These different shapes are achieved by modifying the design of the plastic window 226 in the middle plastic sheet 102.

For practical application, the dynamic fenestration system can be directly attached to the body or limbs of the patient. However, as shown in FIG. 5 it can be attached to a surgical drape 504 or directly to a patient's limb 610 using thin double tape or any suitable tape positioned along the border of the system. This attachment method allows the system to conform to the contours of the surgical drape 504 (FIG. 5) or the patient's body (FIG. 6) while maintaining its functionality.

The operation of the dynamic fenestration system remains consistent whether attached to a surgical drape 504 or directly to a patient. The user controls the opening and closing of the fenestration by manipulating the first end bead 208 and the second end bead 211, providing easy access for wound care and monitoring while maintaining protection against atmospheric contamination when closed.

The dynamic fenestration system accommodates various fenestration configurations to suit different wound types, sizes, and monitoring requirements. FIG. 4A illustrates a square fenestration or window 409 incorporated into the middle plastic sheet 102. The square fenestration 409 provides a uniform viewing area, making it suitable for observing and accessing wounds with relatively symmetrical shapes. In some cases, the square fenestration 409 has dimensions of 150×150 mm, offering a substantial area for wound care and monitoring.

Figure 4B:
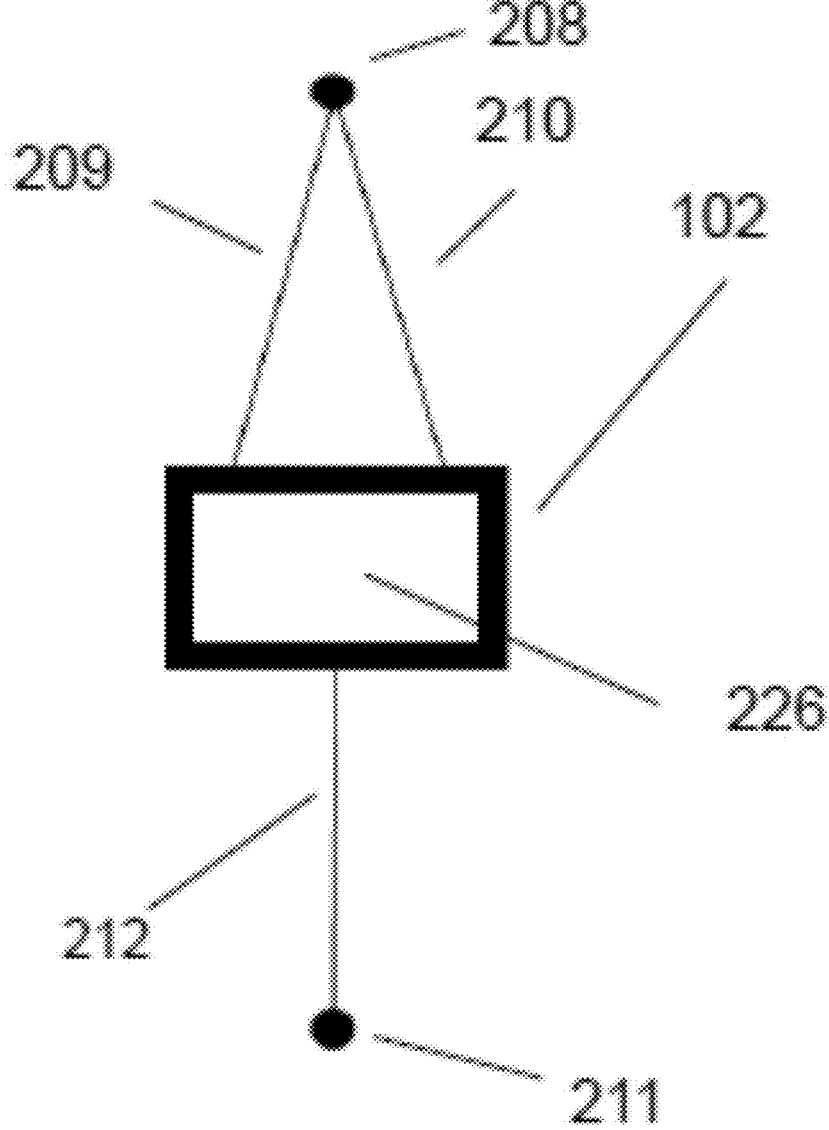
FIG. 4B illustrates a top view of the fenestration device with a rectangular configuration, according to an embodiment.
Figure 4C:
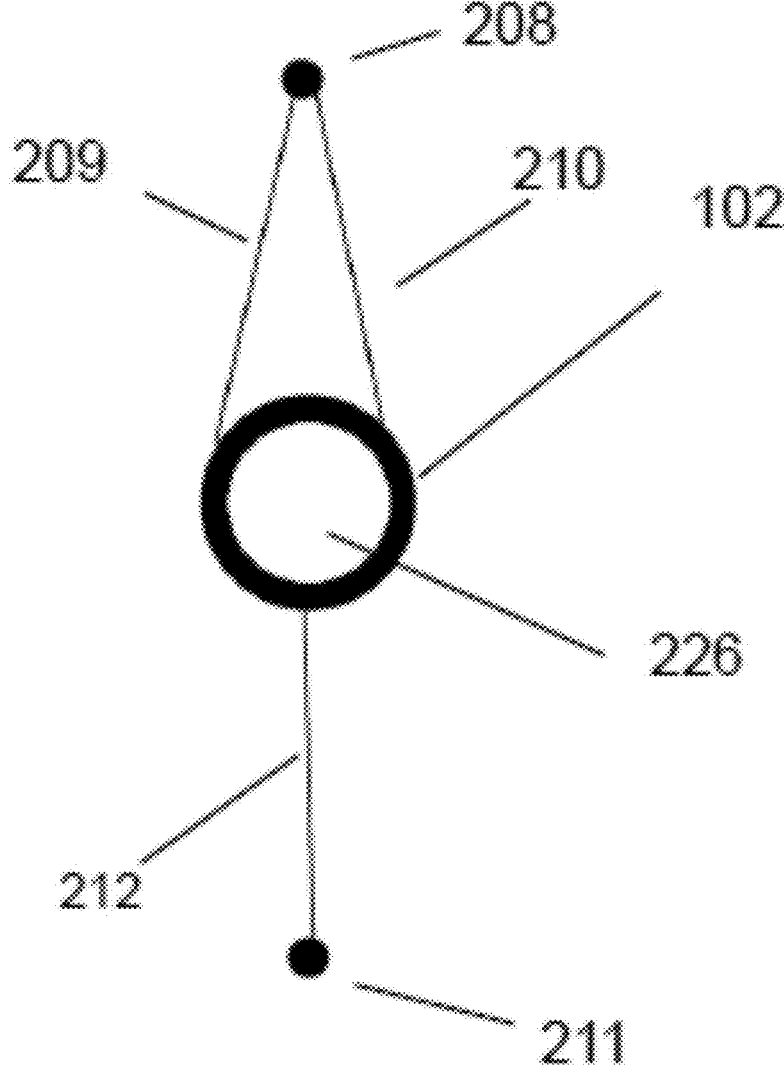
FIG. 4C illustrates a top view of the fenestration device with a circular configuration, according to aspects of the present disclosure.
Figure 4D:
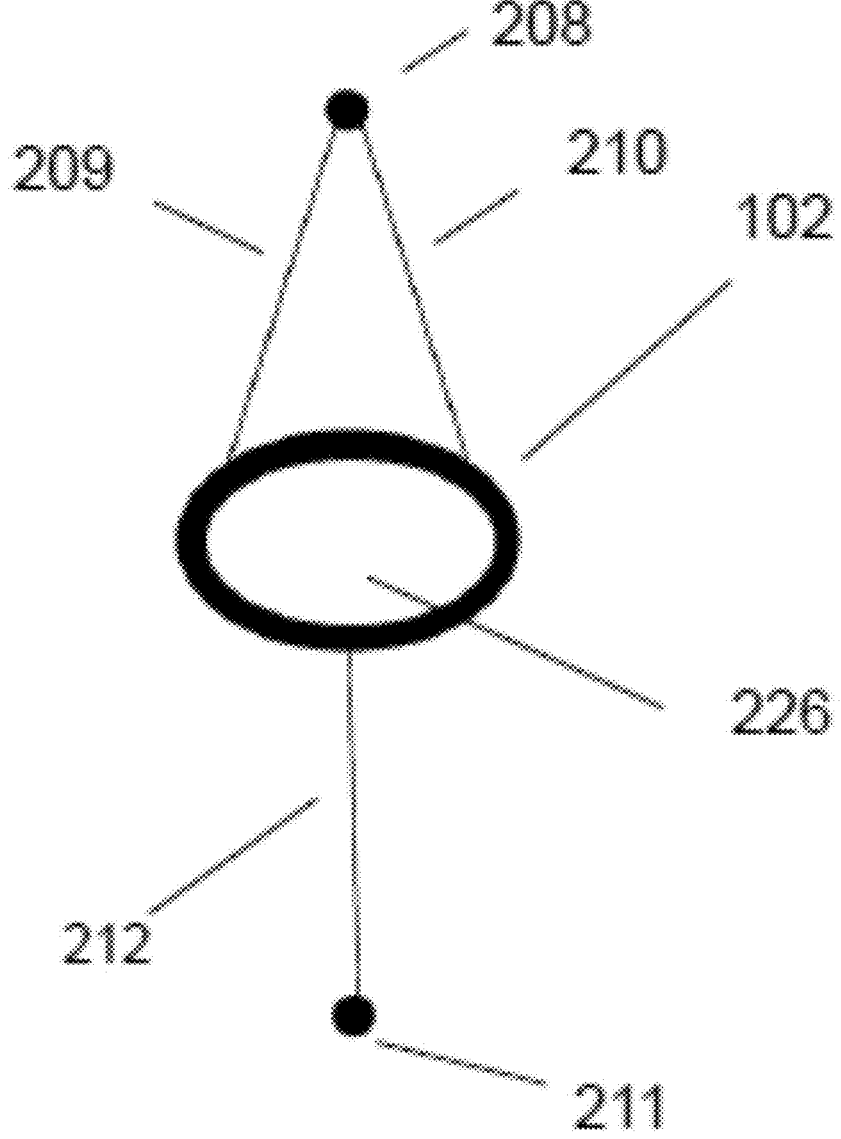
FIG. 4D illustrates a top view of the fenestration device with an oval configuration, according to an embodiment.

FIG. 4B depicts a rectangular fenestration or window 410 integrated into the middle plastic sheet 102. The rectangular fenestration or window 410 is advantageous for elongated wounds or incisions, allowing for a wider field of view along one axis. This configuration is particularly useful for surgical incisions or injuries that extend linearly across the body.

A circular fenestration or window 411 is shown in FIG. 4C, also incorporated into the middle plastic sheet 102. The circular fenestration or window 411 provides a consistent viewing radius from the center point, making it ideal for circular wounds or when a uniform observation area is desired around a central point of interest.

FIG. 4D illustrates an oval fenestration or window 412 in the middle plastic sheet 102. The oval fenestration or window 412 combines aspects of both the rectangular and circular configurations, offering an elongated shape with rounded edges. This configuration is suitable for wounds that are neither perfectly circular nor strictly linear, providing flexibility in coverage and access.

Each fenestration configuration includes the plastic window 226 within the middle frame 125 of the middle plastic sheet 102. The plastic window 226 aligns with corresponding openings in the top plastic sheet 101 and bottom plastic sheet 103 when the fenestration is closed.

For applications requiring a smaller viewing area, such as for use on limbs or in confined spaces, a compact version of the dynamic fenestration system is available. This version features frames with a fenestration of 50×50 mm and top and bottom sheets measuring 200×250 mm. The reduced size allows for easier application and conformity to smaller body areas while maintaining the functionality of the larger system.

The various fenestration configurations are controlled using the same string mechanism described earlier. The first string 209 and second string 210 are attached to the first end bead 208, while the third string 212 is connected to the second end bead 211. These strings enable precise control over the opening and closing of the fenestration, regardless of its shape.

The first lateral seal 204, second lateral seal 205, first alignment seal 206, and second alignment seal 207 work in conjunction with each fenestration configuration to ensure smooth operation and maintain proper alignment of the middle plastic sheet 102 within the system.

By offering multiple fenestration configurations, the dynamic fenestration system provides healthcare professionals with the flexibility to choose the most appropriate shape for specific wound types and monitoring needs, enhancing the system's versatility and effectiveness in various clinical scenarios.

The dynamic fenestration system finds application in various medical scenarios, providing flexibility and functionality across different settings. In sterile operating theaters, the system attaches to surgical drapes, as illustrated in FIG. 5. The top plastic sheet 101, middle plastic sheet 102, and bottom plastic sheet 103 are secured to the surgical drape 504 using thin double-sided tape or any suitable attachment method along the border of the system. This configuration allows healthcare professionals to maintain a sterile field while having controlled access to the surgical site.

When attached to a surgical drape 504, the dynamic fenestration system enables surgeons and medical staff to observe the incision area through the transparent plastic sheets. The plastic window 226 in the middle plastic sheet 102 aligns with corresponding openings in the top plastic sheet 101 and bottom plastic sheet 103 when the fenestration is closed. This alignment creates a clear viewing area for monitoring the surgical site and the ability to easily access the wound without removing the dressing.

In emergency room settings, the dynamic fenestration system is applied directly to patient limbs, as shown in FIG. 6. The system conforms to the contours of the limb 610, providing protection and allowing for continuous observation of injuries or wounds. The flexible nature of the plastic sheets ensures a snug fit around the limb while maintaining the functionality of the fenestration mechanism. In an alternative embodiment the system can be attached directly to the patient or to a surgical drape that covers the patient.

For first responders and in transport situations, the dynamic fenestration system offers protection and monitoring capabilities during patient transfer to medical facilities. The system is designed to be easily applied and operated in challenging environments. The first end bead 208 and second end bead 211, connected to the first string 209, second string 210, and third string 212 respectively, allow for quick and precise control of the fenestration opening and closing.

In all applications, the first lateral seal 204 and second lateral seal 205 limit the range of motion of the middle plastic sheet 102, ensuring controlled movement of the plastic window 226. The first alignment seal 206 and second alignment seal 207 maintain proper alignment during operation, regardless of the application scenario.

The dynamic fenestration system is particularly beneficial in situations where atmospheric contamination is a concern, such as battlefield environments, forest fires, floods, dust storms, or volcanic eruptions. The closed configuration of the system, achieved by sliding the middle plastic sheet 102 to cover the openings in the top plastic sheet 101 and bottom plastic sheet 103, provides a barrier against environmental contaminants while still allowing visual assessment of the protected area.

For pediatric patients or in situations requiring smaller coverage areas, a compact version of the system with reduced dimensions is envisioned. This version maintains the same structural elements, including the top frame 121, middle frame 125, and bottom frame 123, but in a more compact form factor suitable for smaller body areas or confined spaces.

The versatility of the dynamic fenestration system extends to its use in first aid kits. The simplicity of operation makes it suitable for use by individuals without extensive medical training, providing a means to protect and monitor injuries in various emergency situations where professional medical assistance is not immediately available.

In all use cases, the system allows for rapid access to the injured or surgical area when needed. By manipulating the first end bead 208 or second end bead 211, users can quickly open the fenestration by moving the plastic window 226 away from the openings in the top plastic sheet 101 and bottom plastic sheet 103, as depicted in FIG. 3B. Conversely, closing the fenestration is achieved by sliding the middle plastic sheet 102 to cover the openings, as shown in FIG. 3A.

The dynamic fenestration system's design, as illustrated in FIG. 1 and FIG. 2, ensures consistent functionality across various applications. Whether attached to a surgical drape 504 or applied directly to a patient's limb 610, the system maintains its ability to provide protection, allow for continuous monitoring, and enable controlled access to the area of interest.

The dynamic fenestration system is illustrated in detail through a series of figures that demonstrate its structure, components, and functionality.

The instant innovation can further be described as a fenestration system for protecting and monitoring an injured area, comprising:
- a. a first sheet having a first opening;
- b. a second sheet having a second opening aligned with the first opening;
- c. a third transparent sheet positioned between the first and second transparent sheets, the third transparent sheet being movable relative to the first and second transparent sheets and the third transparent sheet comprising of a transparent window; and
- d. at least one non-elastic string coupled to the third transparent sheet for manually moving the third transparent sheet to selectively cover or uncover the first and second openings.

The fenestration system provides a system for protecting and monitoring an injured area wherein the third transparent sheet comprises a plastic window.

The fenestration system provides a system or protecting and monitoring an injured area wherein the plastic window is configured to align with the first and second openings when the third transparent sheet is moved to cover the openings.

The fenestration system provides a system for protecting and monitoring an injured area further comprises a first frame surrounding the first opening and a second frame surrounding the second opening.

The fenestration system provides a system for protecting and monitoring an injured area.

The fenestration system, further comprising at least one lateral seal limiting the range of motion of the third transparent sheet.

The fenestration system provides a system for protecting and monitoring an injured area further comprising at least one alignment seal maintaining proper alignment of the third transparent sheet during movement.

The fenestration system provides a system protecting and monitoring an injured area wherein the at least one non-elastic string comprises a first string attached to a first end of the third transparent sheet and a second string attached to an opposite end of the third transparent sheet.

The fenestration system providing a system or protecting and monitoring an injured area further comprising a first end bead attached to the first string and a second end bead attached to the second string, wherein the end beads facilitate manual movement of the third transparent sheet.

The system being a method of protecting and monitoring an injured area, comprising:
- a. providing a fenestration system having a first transparent sheet with a first opening, a second transparent sheet with a second opening aligned with the first opening, and a third transparent sheet positioned between the first and second transparent sheets;
- b. attaching the fenestration system to a patient or a surgical drape; and
- c. manually moving the third transparent sheet using at least one non-elastic string coupled to the third transparent sheet to selectively cover or uncover the first and second openings.

The fenestration system provides a method of protecting and monitoring an injured area wherein the fenestration system further comprises a plastic window in the third transparent sheet configured to align with the first and second openings when the third transparent sheet is moved to cover the openings.

The fenestration system provides a method of protecting and monitoring an injured area wherein the fenestration system further comprises a first frame surrounding the first opening and a second frame surrounding the second opening.

The fenestration system provides a method of protecting and monitoring an injured area wherein the first and second frames are made of a flexible material.

The fenestration system provides a method of protecting and monitoring an injured area wherein the fenestration system further comprises at least one lateral seal limiting the range of motion of the third transparent sheet.

The fenestration system provides a method of protecting and monitoring an injured area wherein the fenestration system further comprises at least one alignment seal maintaining proper alignment of the third transparent sheet during movement.

The fenestration system provides a method of protecting and monitoring an injured area, wherein the at least one non-elastic string comprises a first string attached to a first end of the third transparent sheet and a second string attached to an opposite end of the third transparent sheet, and wherein the fenestration system further comprises a first end bead attached to the first string and a second end bead attached to the second string to facilitate manual movement of the third transparent sheet.

A wound care kit, comprising:
  a. a fenestration device having a first transparent sheet with a first opening, a second transparent sheet with a second opening aligned with the first opening, and a third transparent sheet positioned between the first and second transparent sheets;
  b. at least one non-elastic string coupled to the third transparent sheet for manually moving the third transparent sheet; and
  c. an adhesive for attaching the fenestration device to a patient or a surgical drape.

The fenestration system provides a wound care kit wherein the fenestration device further comprises a first frame surrounding the first opening and a second frame surrounding the second opening, the first and second frames being made of a flexible material.

The fenestration system provides a wound care kit wherein the fenestration device further comprises at least one lateral seal limiting the range of motion of the third transparent sheet and at least one alignment seal maintaining proper alignment of the third transparent sheet during movement.

The fenestration system provides a wound care kit wherein the at least one non-elastic string comprises a first string attached to a first end of the third transparent sheet and a second string attached to an opposite end of the third transparent sheet, and wherein the fenestration device further comprises a first end bead attached to the first string and a second end bead attached to the second string to facilitate manual movement of the third transparent sheet.

Referring now to the drawings FIGS. 1-6, and more particularly to FIG. 1, there is shown an exploded view of the multi-layer fenestration device. The device comprises three transparent plastic sheets or sheets made from a suitable material and they are arranged in a stacked configuration. The top plastic sheet 101 includes the top frame 121, the middle plastic sheet 102 incorporates the middle frame 125, and the bottom plastic sheet 103 features the bottom frame 123. The middle plastic sheet 102 contains the plastic window 226 within the middle frame 125. The system can also be made using non transparent materials for top plastic sheet 101 and the bottom plastic sheet 103. The transparent access is provided by an opening or hole in the top frame 121 and the bottom frame 123.

The device utilizes a string-based mechanism for controlling the movement of the middle plastic sheet 102. This mechanism includes the first end bead 208 connected to the first string 209 and the second string 210 at one end, while the second end bead 211 is attached to the third string 212 at the opposite end. These strings are connected to the middle plastic sheet 102 to enable manual control of its position.

FIG. 2 illustrates a top view of the fenestration device, showing the arrangement of the multiple transparent plastic sheets and associated components. The top plastic sheet 101, the middle plastic sheet 102, and the bottom plastic sheet 103 are arranged in a layered configuration. The plastic window 226 is incorporated within the middle plastic sheet 102. The top plastic sheet 101 and the bottom plastic sheet 103 can be made from non-transparent material and the transparent access is provided by an opening or hole in the top frame 121 and the bottom frame 123.

The device includes several seals that control and guide the movement of the middle plastic sheet 102. The first lateral seal 204 and the second lateral seal 205 are positioned to limit the range of motion of the middle plastic sheet 102. The first alignment seal 206 and the second alignment seal 207 are arranged to maintain proper alignment during operation.

FIG. 3A and FIG. 3B demonstrate the closed and open positions of the fenestration device, respectively. In FIG. 3A, the plastic window 226 in the middle plastic sheet 102 is centered within the device structure, with the seals and strings configured to allow controlled linear movement. FIG. 3B shows the plastic window 226 offset from openings in the top and bottom layers, creating access through the device.

The system accommodates various fenestration shapes to suit different wound types and sizes. FIG. 4A shows the square fenestration 409, FIG. 4B displays the rectangular fenestration 410, FIG. 4C presents the circular fenestration 411, and FIG. 4D illustrates the oval fenestration 412. Each of these configurations is incorporated into the middle plastic sheet 102 and includes the plastic window 226 within the middle frame 125.

FIG. 5 demonstrates how the fenestration system is designed to be used with the surgical drape 504. The device is shown mounted on the surgical drape 504, with the fenestration system positioned to provide access through the drape while maintaining the ability to protect and observe the area beneath.

FIG. 6 illustrates the application of the fenestration device to a limb 610. The device conforms to the curved surface of the limb while maintaining its functionality for protecting and providing visual access to the underlying area. The bottom plastic sheet 103 features the bottom frame 123 can have lanolin applied to it to lubricate the layers so that the middle sheet can slide over bottom plastic sheet 103 features the bottom frame 123. The Lanolin is natural wax that is extracted from sheep's wool. It contains compounds called lanolin alcohols and wax esters, which also have antimicrobial effects. Studies have shown that lanolin can inhibit the growth of several types of bacteria, including *Staphylococcus aureus* and *Pseudomonas aeruginosa*. The incorporation of lanolin provides two benefits to the system. First it is a lubricant that reduces the frictional forces and second it provides an antibacterial agent to protect the wound from infection.

In some cases, the top plastic sheet 101 and the bottom plastic sheet 103 have dimensions of 350×375 mm. This size provides ample coverage for various wound sizes and types while allowing for easy manipulation of the fenestration device. However, any suitable size is envisioned by the disclosure.

A number of implementations have been described. Nevertheless, it will be understood that various modifications may be made without departing from the spirit and scope of the disclosure. Accordingly, other implementations are within the scope of the following claims.

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

In addition, the present invention has been described with reference to embodiments; it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

Although very narrow claims are presented herein, it should be recognized that the scope of this invention is much broader than presented by the claim. It is intended that broader claims will be submitted in an application that claims the benefit of priority from this application.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A fenestration system for protecting and monitoring an injured area, comprising:

a first sheet having a first opening;

a second sheet having a second opening aligned with the first opening;

a pocket formed between the first and second sheets having an area smaller than the area of the first and second sheets, the pocket being defined by at least one lateral seal and at least one alignment seal;

a third transparent sheet positioned between the first and second sheets, the third transparent sheet being movable within the pocket such that the at least one lateral seal limits the range of motion of the third transparent sheet relative to the first and second sheets and the at least one alignment seal maintains proper alignment of the third transparent sheet during movement; and at least one first non-elastic string coupled to the third transparent sheet at a first end thereof and at least one second non-elastic string attached to an opposite end of the third transparent sheet, the first and second strings extending to allow grasping by a user to manually move the third transparent sheet to selectively cover or uncover the first and second openings.

2. The fenestration system of claim 1, wherein the third transparent sheet comprises a transparent plastic window.

3. The fenestration system of claim 2, wherein the transparent plastic window is configured to align within the first and second openings when the third transparent sheet is moved within the pocket to cover the openings.

4. The fenestration system of claim 1, further comprising a first frame surrounding the first opening and a second frame surrounding the second opening.

5. The fenestration system of claim 4, wherein the first and second frames are made of a flexible material.

6. The fenestration system of claim 1, further comprising a first end bead attached to the at least one first non-elastic string and a second end bead attached to the at least one second non-elastic string, wherein the first and second end beads facilitate grasping by a user to manually move the third transparent sheet.

7. The fenestration system of claim 1, wherein the first sheet and the second sheet are transparent.

8. The fenestration system of claim 1, wherein the at least one first string further comprises at least two first strings that each attach at one end to the transparent middle sheet on the same end thereof, at spaced apart locations, and which attach together at their other ends.

9. A method of protecting and monitoring an injured area, comprising:

providing a fenestration system having a first sheet having a first opening, a second sheet having a second opening aligned with the first opening, a pocket formed between the first and second sheets having an area smaller than the area of the first and second sheets, the pocket being defined by at least one lateral seal and at least one alignment seal, and a third transparent sheet positioned in the pocket such that the at least one lateral seal limits the range of motion of the third transparent sheet relative to the first and second sheets and the at least one alignment seal maintains proper alignment of the third transparent sheet during movement, and at least one first non-elastic string and at least one second non-elastic string, the first and second strings being coupled to the third transparent sheet at either end thereof to facilitate moving the third transparent sheet in the pocket relative to the first and second sheets;

attaching the fenestration system to a patient or a surgical drape; and manually moving the third transparent sheet using the at least one first non-elastic string and the at least one second non-elastic string to selectively cover or uncover the first and second openings.

10. The method of claim 9, wherein the fenestration system further comprises a transparent plastic window in the third transparent sheet configured to align with the first and second openings when the third transparent sheet is moved within the pocket to cover the openings.

11. The method of claim 10, wherein the method further comprises a first frame surrounding the first opening and a second frame surrounding the second opening.

12. The method of claim 11, wherein the first and second frames are made of a flexible material.

13. The method of claim 9, wherein the fenestration system further comprises a first end bead attached to the at least one first string and a second end bead attached to the at least one second string, the first and second end beads facilitating manual movement of the third transparent sheet.

14. The method of claim 9, wherein the first sheet and the second sheet are transparent.

15. The method of claim 9, wherein the at least one first string further comprises at least two first strings that each attach at one end to the transparent middle sheet on the same end thereof, at spaced apart locations, and which attach together at their other ends.

16. A wound care kit, comprising:

a fenestration device having a first sheet having a first opening, a second sheet having a second opening aligned with the first opening, a pocket formed between the first and second sheets having an area smaller than the area of the first and second sheets, the pocket being defined by at least one lateral seal and at least one alignment seal, and a third transparent sheet positioned in the pocket such that the at least one lateral seal limits the range of motion of the third transparent sheet relative to the first and second sheets and the at least one alignment seal maintains proper alignment of the third transparent sheet during movement;

at least one first non-elastic string coupled to the third transparent sheet at a first end thereof and at least one second non-elastic string attached to an opposite end of the third transparent sheet, the first and second strings extending to allow grasping by a user to manually move the third transparent sheet inside the pocket to selectively cover or uncover the first and second openings; and an adhesive for attaching the fenestration device to a patient or a surgical drape.

17. The wound care kit of claim 16, wherein the fenestration device further comprises a first frame surrounding the first opening and a second frame surrounding the second opening, the first and second frames being made of a flexible material.

18. The wound care kit of claim 16 wherein the fenestration device further comprises a first end bead attached to the at least one first non-elastic string and a second end bead attached to the at least one second non-elastic string, the first and second end beads facilitating manual movement of the third transparent sheet.

19. The wound care kit of claim 16, wherein the first sheet and the second sheet are transparent.

20. The wound care kit of claim 16, wherein the at least one first string further comprises at least two first strings that each attach at one end to the transparent middle sheet on the same end thereof, at spaced apart locations, and which attach together at their other ends.

* * * * *